United States Patent [19]

Sarr

[11] Patent Number: 4,799,177

[45] Date of Patent: Jan. 17, 1989

[54] ULTRASONIC INSTRUMENTATION FOR EXAMINATION OF VARIABLE-THICKNESS OBJECTS

[75] Inventor: Dennis P. Sarr, Kent, Wash.

[73] Assignee: The Boeing Company, Seattle, Wash.

[21] Appl. No.: 815,038

[22] Filed: Dec. 31, 1985

[51] Int. Cl.$^4$ .......................................... G01N 29/00
[52] U.S. Cl. .................................. 364/563; 364/552; 73/625; 73/628
[58] Field of Search ............... 364/503, 506, 507, 552, 364/570; 73/610, 611, 612, 622, 624, 625, 628, 636, 644, 598

[56] References Cited

U.S. PATENT DOCUMENTS

| | | | |
|---|---|---|---|
| 2,430,013 | 11/1947 | Hansell . | |
| 2,477,246 | 7/1949 | Gillespie . | |
| 2,481,068 | 9/1949 | Best . | |
| 3,051,956 | 8/1962 | Theobald . | |
| 3,059,228 | 10/1962 | Beck et al. | 340/179 |
| 3,086,195 | 4/1963 | Halliday | 340/15 |
| 3,166,731 | 1/1965 | Joy | 340/15 |
| 3,255,417 | 6/1966 | Gottlieb | 328/145 |
| 3,363,226 | 1/1968 | Murphree . | |
| 3,364,466 | 1/1968 | Stine | 340/147 |
| 3,524,162 | 8/1970 | Zill | 340/15.5 |
| 3,570,279 | 3/1971 | Davies . | |
| 3,575,043 | 4/1971 | Allen et al. | 73/67.8 |
| 3,585,509 | 6/1971 | Davis et al. | 328/145 |
| 3,624,370 | 11/1971 | Gray, Jr. . | |
| 3,633,211 | 1/1972 | Batzdorff . | |
| 3,649,826 | 3/1972 | Larsson et al. | 235/197 |
| 3,662,274 | 5/1972 | Pritchard et al. | 329/192 |
| 3,663,842 | 5/1972 | Miller | 73/642 |
| 3,675,472 | 7/1972 | Kay et al. | 73/67.5 R |
| 3,687,219 | 8/1972 | Langlois . | |
| 3,704,425 | 11/1972 | Haigh | 328/145 |
| 3,712,989 | 1/1973 | Barton | 307/235 |
| 3,792,613 | 2/1974 | Couture | 73/67.9 |
| 3,815,144 | 6/1974 | Aiken . | |
| 3,857,052 | 12/1974 | Beller | 340/149 R |
| 3,875,381 | 4/1975 | Wingfield et al. | 235/151.3 |
| 3,881,466 | 5/1975 | Wilcox | 128/2 |
| 3,885,224 | 5/1975 | Klahr . | |
| 3,896,662 | 7/1975 | Camp et al. | 73/67.5 R |
| 3,911,730 | 10/1975 | Niklas | 73/67.7 |
| 3,942,149 | 3/1976 | Westfall, Jr. . | |
| 3,958,451 | 5/1976 | Richardson | 73/67.8 S |
| 3,958,559 | 5/1976 | Glenn et al. | 73/642 |
| 3,959,732 | 5/1976 | Schaefer | 328/151 |
| 3,959,770 | 5/1976 | Schaefer | 340/146.1 E |
| 3,961,523 | 6/1976 | Cornforth | 73/622 |
| 3,981,184 | 9/1976 | Matay | 364/552 |
| 3,986,011 | 10/1976 | Poole et al. . | |
| 3,986,389 | 10/1976 | Mesina et al. | 73/611 |
| 4,012,952 | 3/1977 | Dory | 73/67.7 |
| 4,038,664 | 7/1977 | Muir . | |
| 4,050,057 | 9/1977 | Backman, Jr. . | |
| 4,055,989 | 11/1977 | Henry, Jr. et al. | 73/622 |
| 4,070,905 | 1/1978 | Kassoff | 73/614 |
| 4,088,028 | 5/1978 | Hildebrandt | 364/507 |
| 4,096,484 | 6/1978 | Ferre et al. . | |
| 4,102,205 | 7/1978 | Pies et al. | 73/626 |
| 4,138,248 | 2/1979 | Narain | 75/101 R |
| 4,144,508 | 3/1979 | Lewis et al. . | |
| 4,145,680 | 3/1979 | Smith | 340/5 MP |
| 4,146,750 | 3/1979 | Spiesman | 370/112 |
| 4,147,065 | 4/1979 | Lather et al. | 73/611 |
| 4,150,577 | 4/1979 | Fetheroff | 73/611 |
| 4,160,385 | 7/1979 | Gromlich et al. | 73/622 |
| 4,160,386 | 7/1979 | Jackson et al. | 73/625 |
| 4,167,121 | 9/1979 | Mauch | 73/640 |

(List continued on next page.)

FOREIGN PATENT DOCUMENTS

| | | | |
|---|---|---|---|
| 0063560 | 4/1984 | Japan | 73/618 |
| 2093185 | 8/1982 | United Kingdom | 73/610 |

*Primary Examiner*—Parshotam S. Lall
*Assistant Examiner*—V. N. Trans
*Attorney, Agent, or Firm*—Finnegan, Henderson, Farabow, Garrett & Dunner

[57] ABSTRACT

Ultrasonic apparatus and methods for detecting defects in a part include a plurality of transducer channels, at least one of which is dedicated to determining the thickness of the part. An initial thickness value is determined and stored, and then subsequent thickness estimates are compared to the original thickness value and, if the estimates bear a predetermined relationship with the stored thickness value, then the thickness estimates become the new thickness values.

26 Claims, 11 Drawing Sheets

U.S. PATENT DOCUMENTS

| | | | |
|---|---|---|---|
| 4,167,753 | 9/1979 | Lynk | 358/140 |
| 4,170,142 | 10/1979 | Posakony et al. | 73/603 |
| 4,172,386 | 10/1979 | Cribbs et al. | 73/618 |
| 4,173,007 | 10/1979 | McKeighen et al. | 367/11 |
| 4,173,897 | 11/1979 | Forstermann et al. | 73/609 |
| 4,173,898 | 11/1979 | Forstermann et al. | 73/611 |
| 4,183,249 | 1/1980 | Anderson | 73/626 |
| 4,184,374 | 1/1980 | Thompson et al. | 73/640 |
| 4,205,395 | 5/1980 | Shortridge | |
| 4,205,686 | 6/1980 | Harris et al. | 73/644 |
| 4,207,620 | 6/1980 | Morgera | |
| 4,208,916 | 6/1980 | Thomenius et al. | 73/626 |
| 4,213,183 | 7/1980 | Barron et al. | 364/507 |
| 4,222,275 | 9/1980 | Shall et al. | 73/636 |
| 4,224,672 | 9/1980 | Leleu et al. | |
| 4,229,796 | 10/1980 | Garrett | 364/507 |
| 4,241,608 | 12/1980 | Dees et al. | 73/606 |
| 4,253,238 | 3/1981 | Iinuma et al. | 73/626 |
| 4,261,040 | 4/1981 | Weidman et al. | 364/554 |
| 4,274,289 | 6/1981 | Weiss et al. | 73/618 |
| 4,284,094 | 8/1981 | Behrend | |
| 4,290,308 | 9/1981 | Dau | |
| 4,310,853 | 1/1982 | Madson | 358/140 |
| 4,327,588 | 5/1982 | North | 364/507 |
| 4,354,388 | 10/1982 | Diepers et al. | 73/612 |
| 4,362,995 | 12/1982 | Morris | 328/145 |
| 4,368,643 | 1/1983 | Tachita et al. | 73/626 |
| 4,373,395 | 2/1983 | Borburgh | 73/607 |
| 4,387,597 | 6/1983 | Brandestini | 73/626 |
| 4,392,379 | 7/1983 | Yamaguchi | 73/626 |
| 4,409,683 | 10/1983 | Woodward | 370/112 |
| 4,417,475 | 11/1983 | Okazaki | 73/626 |
| 4,431,007 | 2/1984 | Amazeen et al. | 128/660 |
| 4,437,332 | 3/1984 | Pittaro | 73/624 |
| 4,446,715 | 5/1984 | Bailey | 364/571 |
| 4,448,076 | 5/1984 | Van Hellsbergen | 73/628 |
| 4,456,982 | 6/1984 | Tournois | 73/624 |
| 4,462,082 | 7/1984 | Thiele et al. | 364/507 |
| 4,470,304 | 9/1984 | Nusbickel, Jr. et al. | 73/611 |
| 4,475,399 | 10/1984 | Livingston | 73/622 |
| 4,524,622 | 6/1985 | Suzuki et al. | 73/640 |
| 4,557,146 | 12/1985 | Buffington et al. | 73/642 |
| 4,558,598 | 12/1985 | Young | 73/644 |
| 4,616,152 | 10/1986 | Saito et al. | 310/327 |
| 4,635,484 | 1/1987 | Lerch | 73/625 |
| 4,660,419 | 4/1987 | Derkocs et al. | 73/622 |

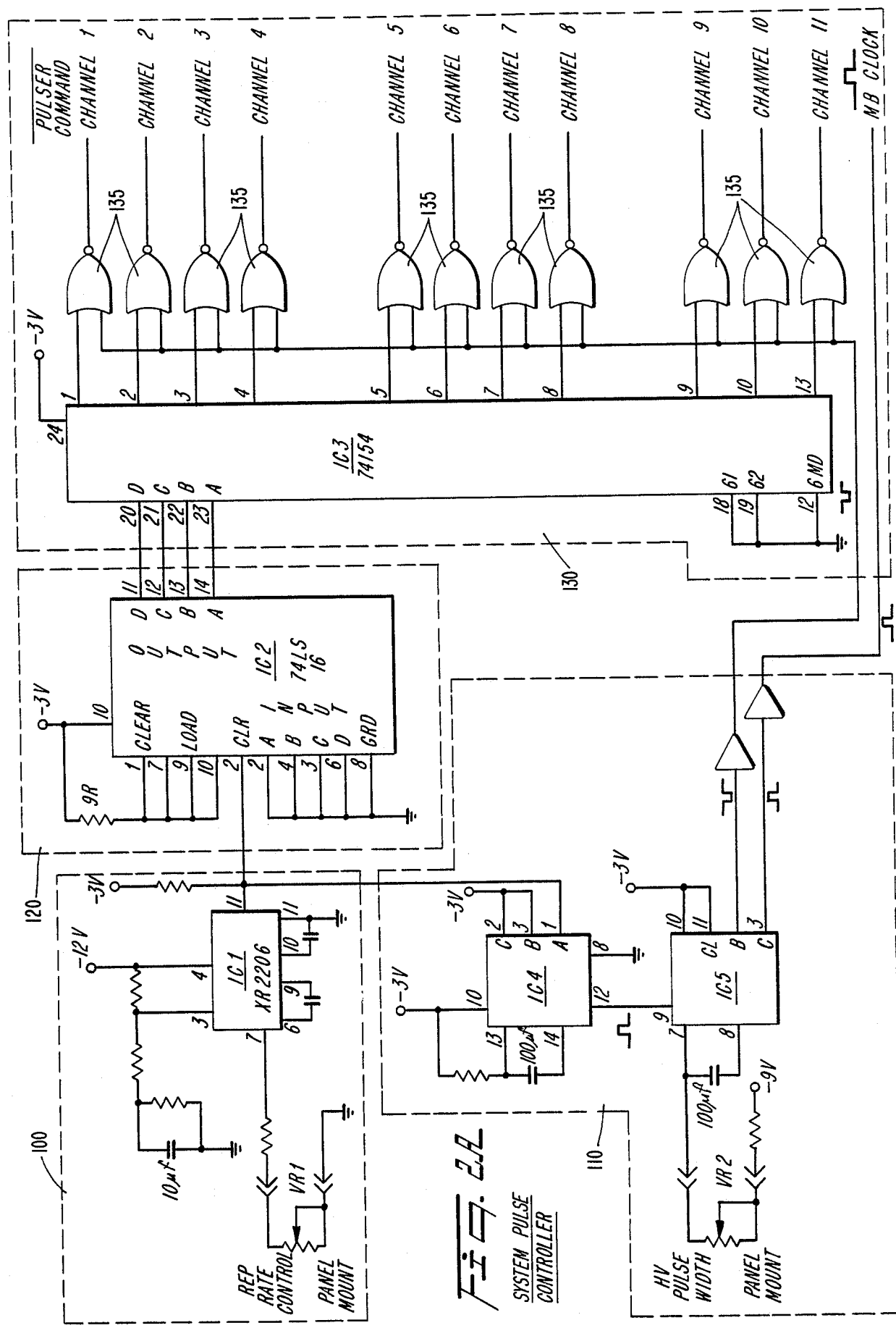
FIG. 2A SYSTEM PULSE CONTROLLER

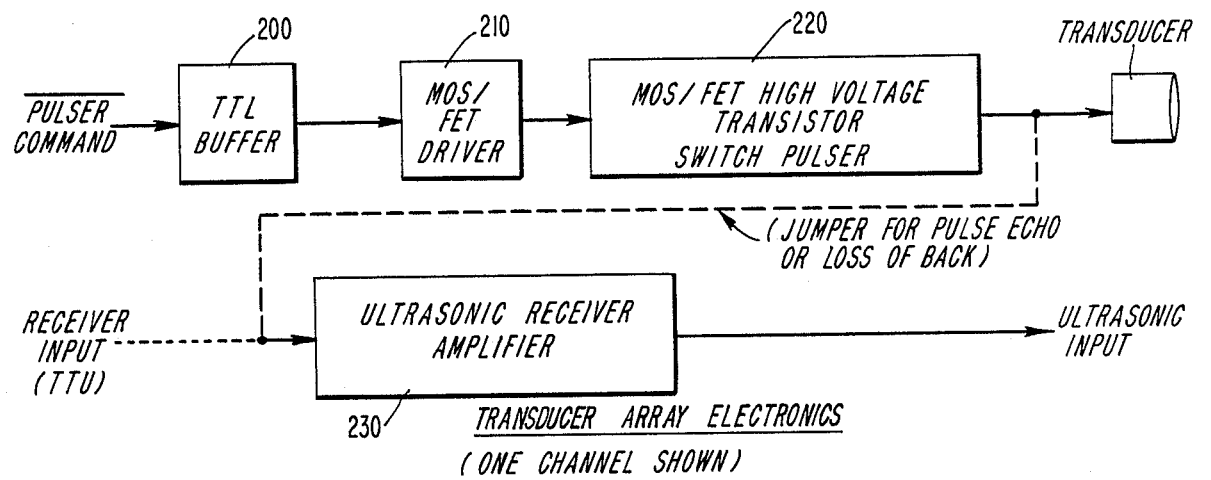
Fig. 3
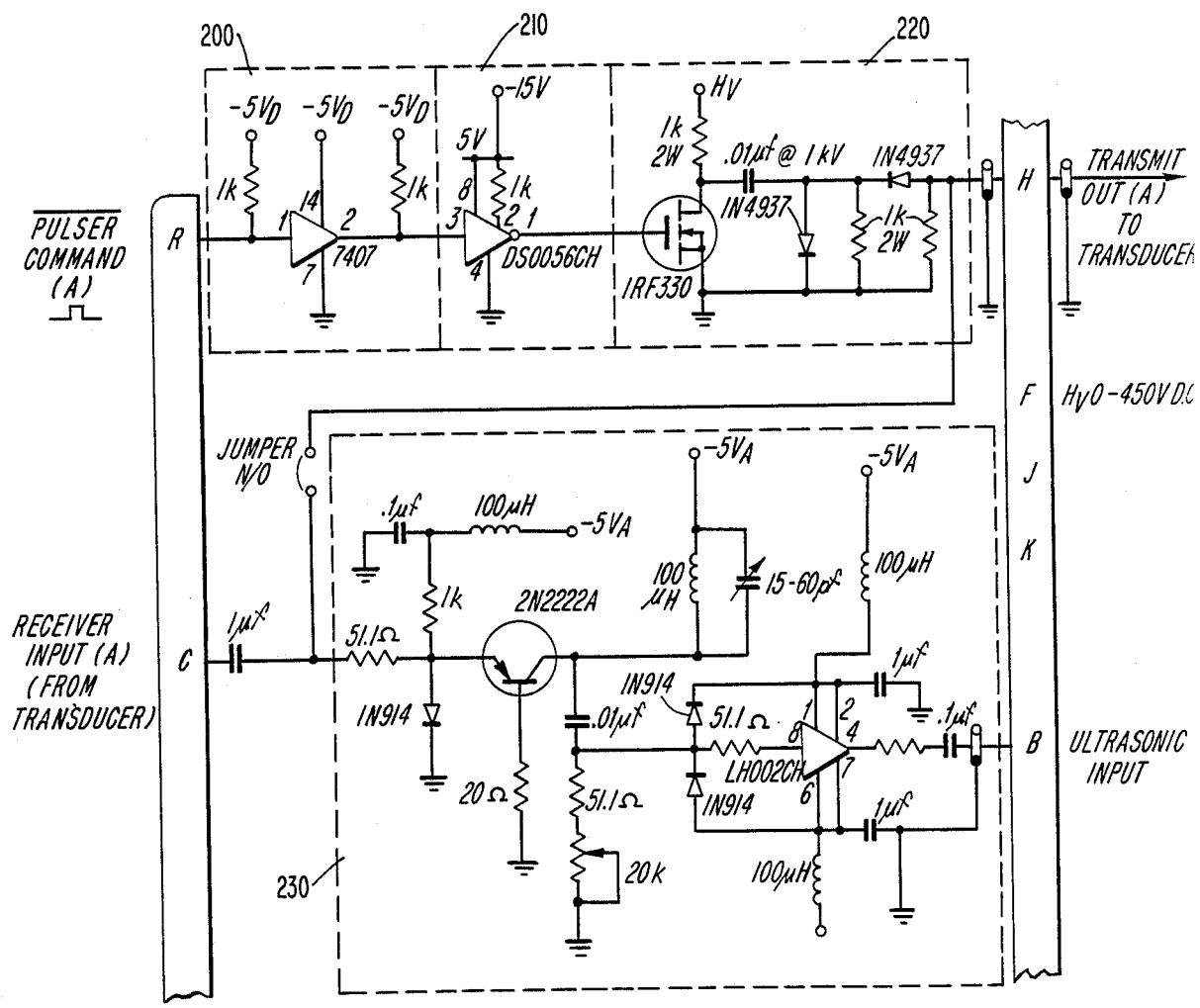
Fig. 3A  TRANSDUCER ARRAY ELECTRONICS

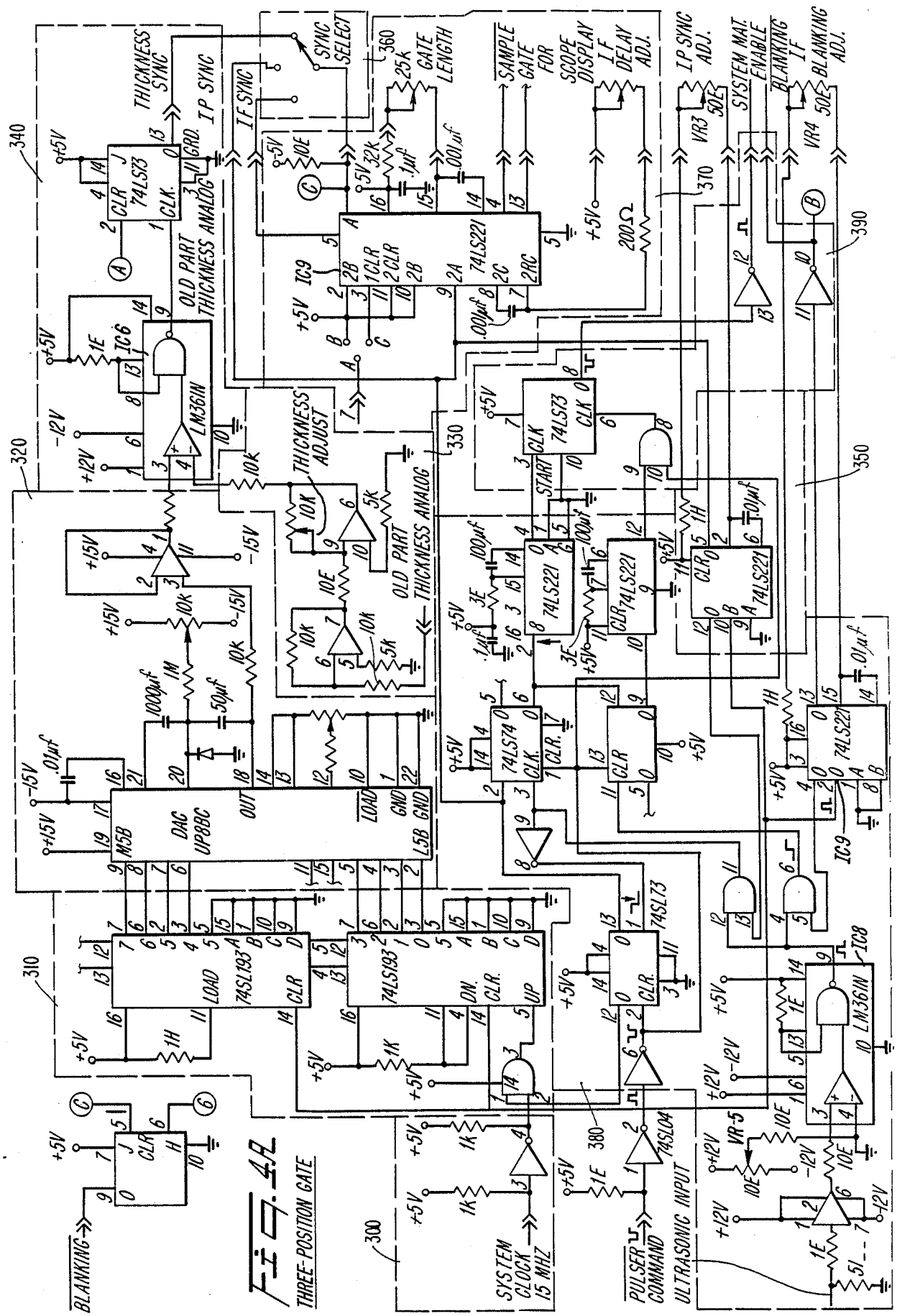

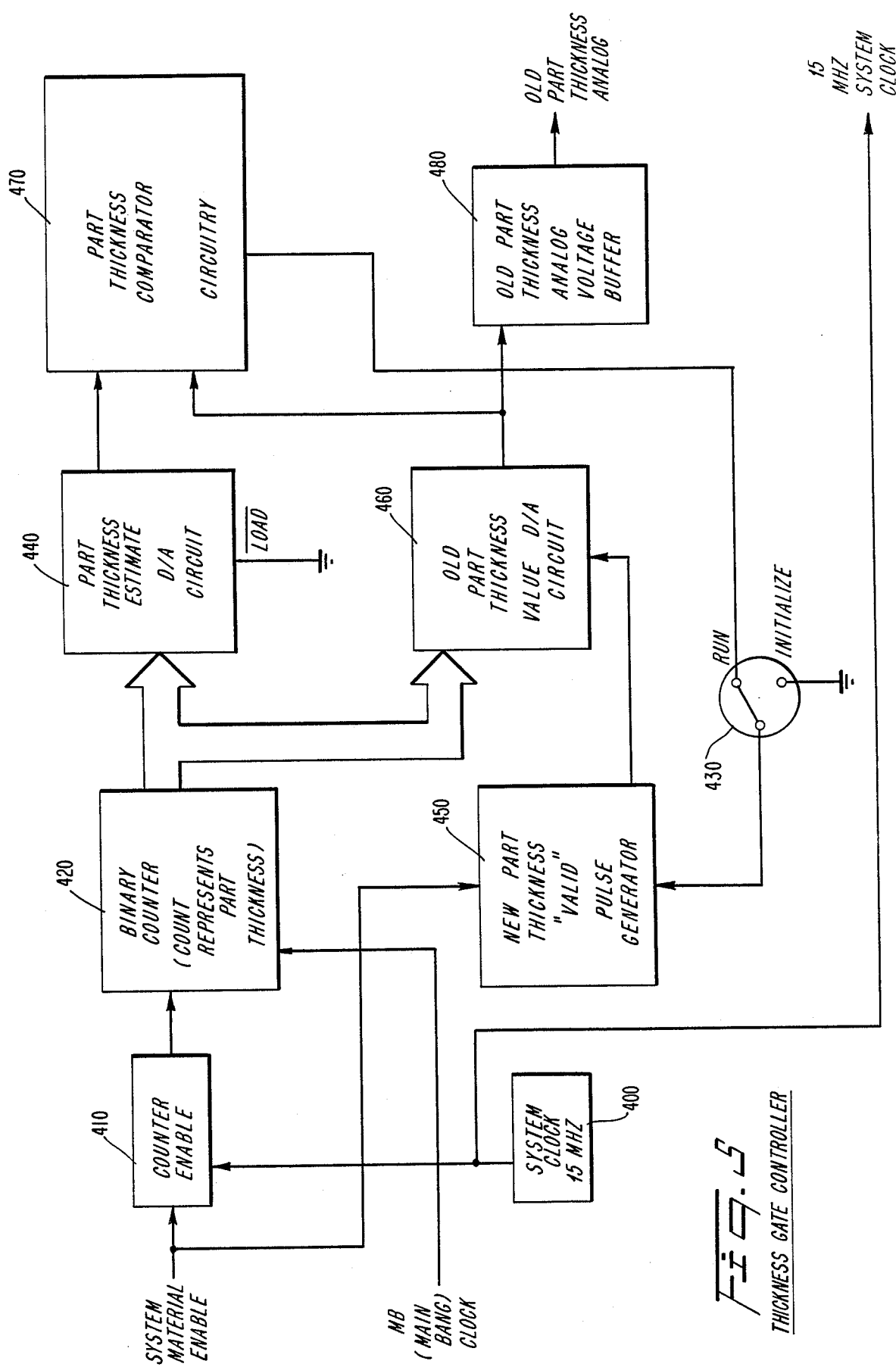

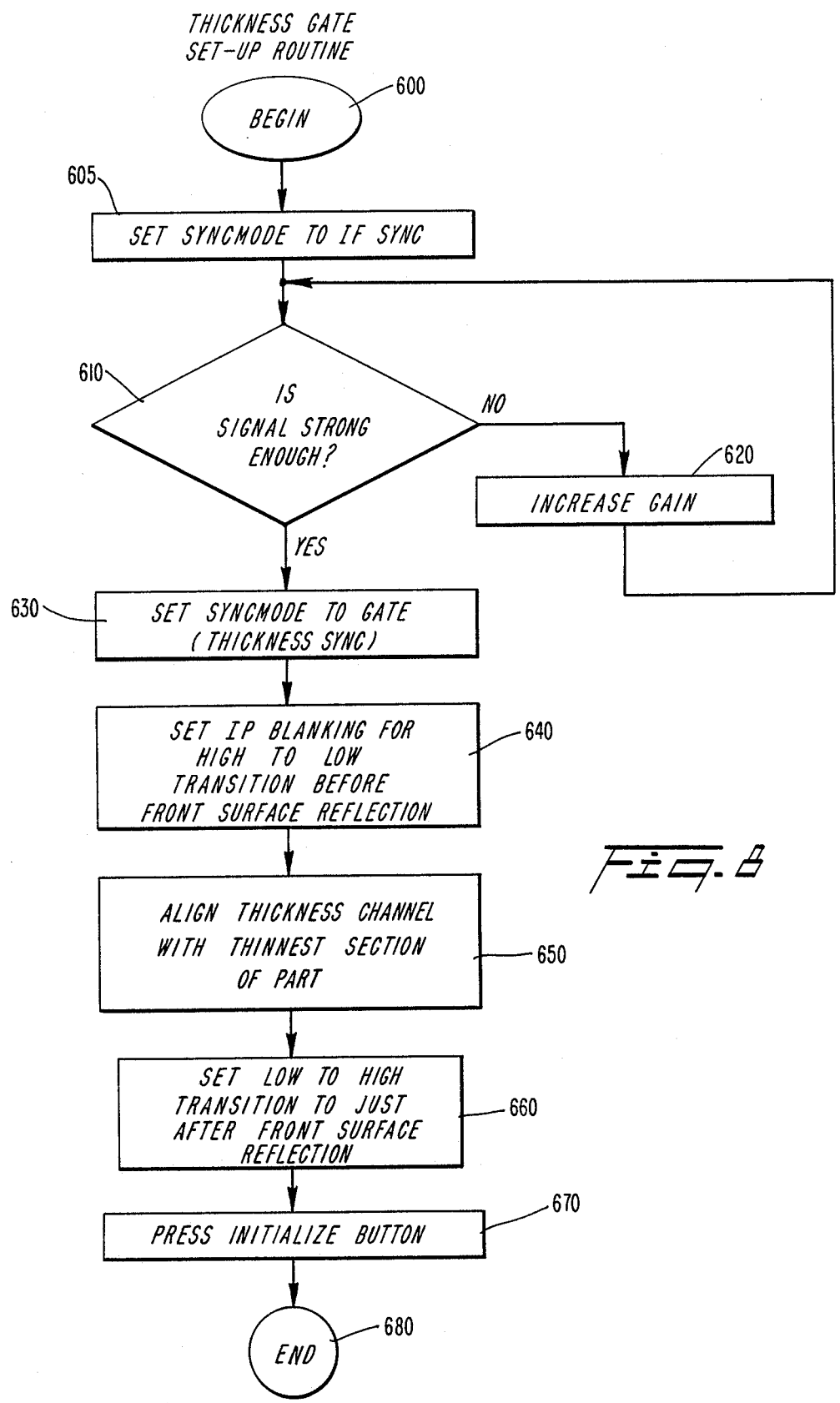

ULTRASONIC INSTRUMENTATION FOR EXAMINATION OF VARIABLE-THICKNESS OBJECTS

CROSS REFERENCE TO RELATED APPLICATIONS

The invention is related to the following copending U.S. patent applications assigned to the assignee of the present invention:
DATA RECORDING APPARATUS FOR AN ULTRASONIC INSPECTION SYSTEM, Ser. No. 06/815,050, filed on Dec. 31, 1985 by D. P. Sarr;
ULTRASONIC INSPECTION SYSTEM WITH LINEAR TRANSDUCER ARRAY, Ser. No. 06/815,047, filed on Dec. 31, 1985 by D. P. Sarr and F. D. Young;
ULTRASONIC INSPECTION SYSTEM APPARATUS AND METHOD, Ser. No. 06/815,048, filed on Dec. 31, 1985 by D. P. Sarr;
AN IMPROVED ULTRASONIC TESTING APPARATUS, Ser. No. 06/815,163, filed Dec. 31, 1985 by G. A. Geithman and D. P. Sarr;
ULTRASONIC TRANSDUCER WITH SHAPED BEAM INTENSITY PROFILE, Ser. No. 06/815,162, filed Dec. 31, 1985 by G. A. Geithman and D. H. Gilbert, now U.S. Pat. No. 4,700,575; and
ULTRASONIC 64 CHANNEL INSPECTION SYSTEM WITH MULTIGATE/MULTI MODE SELECTION SOFTWARE CONFIGURABILITY, Ser. No. 06/815,044, filed Dec. 31, 1985 by D. P. Sarr.

BACKGROUND OF THE INVENTION

The present invention relates to the field of ultrasonic defect detecting systems, and especially to such systems which are used for nondestructive inspection (NDI) of elements having varying thicknesses. This invention has particular application in the testing of aircraft structures made from graphite/epoxy materials.

There are three major types of NDI systems which are used for testing elements, for example, aircraft parts: loss-of-back (LOB), pulse echo (PE) and through transmission ultrasonic (TTU). The LOB technique compares a predetermined threshold value with the peak amplitude of the ultrasonic reflections from an element's rear surface, i.e., the surface most distant from the ultrasonic transducers. If the element has no defects in the volume between the front and back surfaces proximate the transducers, then the peak amplitude of the reflections from the back surface should exceed the threshold. If a defect is present in that volume, the peak amplitude of the signal reflected by the rear surface decreases significantly, in fact below the threshold, because the defect reflects much of the ultrasonic energy before it ever reaches the rear surface.

FIGS. 1A and 1B, which show voltage signals corresponding to ultrasonic reflections from an element having no defects and having a defect, respectively, illustrate this phenomenon. There are three major reflection portions in FIG. 1A. The portion that occurs first, which is the leftmost in FIG. 1A, is an artifact from the ultrasonic pulse transmitted toward the element (sometimes called the "Main Bang"). The next major portion is a reflection from the front surface of the element. The third major portion (the rightmost) is a reflection from the rear surface. Since FIG. 1A corresponds to the reflections received from an element with no defects, the peak amplitude of the reflections from the rear surface is above the predetermined threshold $V_N$, thereby indicating the absence of any defects.

In FIG. 1B, there are four major signal portions proceeding in order from left to right corresponding in time to their receipt by an ultrasonic transducer. The first, and largest, is the artifact from the Main Bang, the second represents a reflection from the front surface of a part, the third represents a reflection from a defect in the interior of the part, and the fourth represents a reflection from the rear surface of the part. Because the defect reflects some of the ultrasonic energy that penetrates the front surface, a smaller amount of energy is available to be reflected from the rear surface. As FIG. 1B shows, that rear surface reflection is below the predetermined threshold $V_N$, so the presence of a defect is noted.

FIGS. 1A and 1B also show the concept of a time window which is used for finding the proper signals for testing. The time period denoted $T_R$ indicates a time window during which reflections or transmitted signals from the rear surface are expected to be received. It is important in the LOB technique to know when that window should begin and end to ensure that the reflections being examined are those from the rear surface, and not those from a defect or the front surface.

The PE technique bears some similarity to the LOB technique. However, instead of examining the peak amplitude of the rear surface reflection as the LOB technique requires, the PE techniques tests the peak amplitudes of the reflections from the element's interior, i.e., from between the front and rear surfaces. If any reflections from the interior above a certain threshold level are received, those reflections are evidence of a defect. If no sufficiently large reflections are received from the element interior, then the element portion under investigation is deemed defect-free.

The TTU technique differs from the above techniques in that it requires two transducers for each transducer channel, the transducers being located on opposite sides of the element to be examined. Instead of examining ultrasonic reflections, however, the TTU technique involves determining the amount of ultrasonic energy that was able to pass entirely through the part.

As the above methods indicate, it is extremely important to control the time window in which the examination takes place. For example, in the LOB method, the time window must be such as to capture only reflections from the rear surface (see $T_R$ in FIGS. 1A and 1B). In the PE method, it is extremely important to obtain a time window that captures reflections between the front and rear surfaces, and which does not include reflections from either of those surfaces (see time window $T_I$ in FIGS. 1A and 1B).

It is not difficult to identify the reflection from the front surface because that is the first reflection that occurs after the Main Bang artifact. If the element being examined has a varying thickness, however, it becomes very difficult to determine where the rear surface is because the location of that surface changes in relation to the front surface, and hence the corresponding time windows related to the rear surface must also change. Furthermore, the only ultrasonic information which is available to find the rear surface are the reflections from the part under test. However, as FIGS. 1A and 1B show, the reflections from a defect and from a rear surface appear very similar. Furthermore, by the time a reflection is properly identified, the ultrasonic detector is usually making another measurement.

One solution to this problem has been to determine thickness mechanically with a calibrated roller, for example. Rollers, however, react slowly and are inaccurate not only because they may lose contact with the surface, but also because the rollers experience wear which gradually makes their measurements imprecise. In addition, rollers cannot be used in many instances. For example, an element may be mounted or configured in a manner to preclude the use of a roller, or the temperature of the elements, for example molten steel sheets, may be too extreme for rollers.

Another way of solving the problem was discussed in U.S. Pat. No. 3,942,358 to Pies. The device in this patent includes an array of transducers which both transmit and receive ultrasonic pulses in the PE mode. The transducers are coupled to electric circuitry which measures the time difference between receipt of the surface reflection and the next major reflection, and then finds the maximum time difference. That maximum time difference is stored and compared to the maximum speed elapsed times determined from succeeding scans. Whenever a maximum time measurement from a succeeding scan exceeds the stored amount, the new maximum time is stored in place of the old value. The result of the entire operation is that the maximum time difference for the entire element, and hence the maximum thickness, is stored and used to set a time window corresponding to the rear surface.

In this system, however, two ultrasonic scans need to be made for each element. The first scan determines the maximum thickness, and the second scan then looks for defects. In addition, since each transducer channel is used for determining thickness during one scan and defects during the next scan, the electronics of this system can become rather complex.

Pies does recognize that for elements of varying thickness, the transmit times could be updated during the scans. This still results in complicated circuitry, however, to perform the thickness measurement task. The system in Pies also cannot detect extensive defects.

It is therefore an object of this invention to provide fast and accurate NDI ultrasonic testing of parts.

Another object of this invention is accurate NDI testing without the use of complicated circuitry.

SUMMARY OF THE INVENTION

The present invention overcomes the problems of the prior art and achieves the objects of this invention with NDI testing apparatus and methods employing a plurality of transducer channels for examining the signals reflected from or transmitted through a part under test. At least one of those channels is dedicated to making thickness measurements by examining reflections from the front and rear surfaces. If the dedicated thickness channel(s) makes a thickness measurement which differs from a current thickness value by less than some predetermined amount, then that new measurement replaces the old thickness value, since it is assumed that the new measurement reflects a thickness change which is relatively slow. If the thickness channel measurement differs from the current thickness value by greater than the predetermined amount, then it is assumed that the second reflection received was not from the rear surface, but rather from a defect in the interior of the element, and the current thickness value remains unchanged.

To achieve the objects and in accordance with the purposes of this invention, as embodied and as broadly described herein, the apparatus of this invention for ultrasonic inspection of a part comprises means for generating a transmission signal; a plurality of transducer channels, coupled to the transmission signal generating means, for generating ultrasonic pulses for transmission into said part, for receiving portions of said ultrasonic pulses, and for creating electrical reflection signals representing said portions, one of the transducer channels being a thickness transducer channel and including means for determining a value representing the thickness of a portion of the part adjacent to the thickness transducer channel; means, coupled to each of the transducer channels, for measuring the amplitude of the electrical reflection signals only during a time window corresponding to the part thickness value; and thickness gating means, coupled to the measuring means, for automatically adjusting the thickness value, and thereby the time window, according to the electrical reflection signals received by the thickness transducer channel.

A method of ultrasonic inspection of a part according to this invention comprises the steps of generating a transmission signal; transmitting ultrasonic pulses into the part using a plurality of transducer channels; receiving and transducing portions of that transmitted ultrasonic pulse and creating electrical reflection signals representing those portions; measuring the amplitude of the electrical reflection channels only during a time window corresponding to a part thickness value; and determining a part thickness value by examining the electrical reflection signals from one channel of the apparatus.

The accompanying drawings, which are incorporated in and which constitute a part of the specification, illustrate one embodiment of the invention and, together with the description, explain the principles of the invention.

BRIEF DESCRIPTION OF THE DRAWINGS

FIGS. 2 and 2A are a block diagram and a detailed circuit diagram, respectively, of a System Pulse Controller of an embodiment of the present invention;

FIGS. 3 and 3A are a block diagram and a detailed circuit diagram, respectively, of a Transducer Array Electronics unit of the embodiment of the present invention;

FIGS. 4 and 4A are a block diagram and a detailed circuit diagram, respectively, of a Three-position Gate of the embodiment of the present invention;

FIGS. 5 and 5A are a block diagram and a detailed circuit diagram, respectively, of a Thickness Gate Controller of the present invention;

FIG. 8 is a flow chart for an initialization routine of the embodiment of the present invention.

DESCRIPTION OF THE PREFERRED EMBODIMENT

Reference is now made in detail to a presently preferred embodiment of the invention, an example of which is illustrated in the accompanying drawings. The embodiment shown relates to an LOB apparatus. Pesrons of ordinary skill in the art will recognize the applicability of the invention to the PE and TTU systems for nondestructive inspection.

Figure 6:
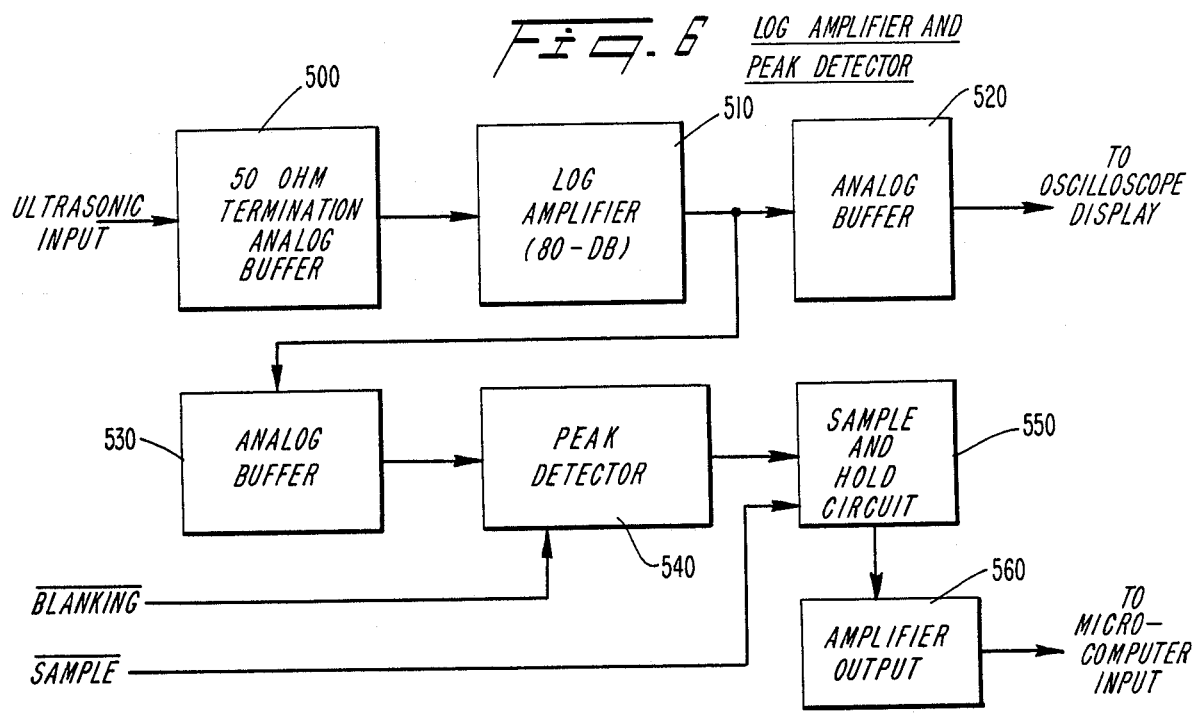
FIGS. 6 and 6A are a block diagram and a detailed circuit diagram, respectively, of a Log Amplifier and Peak Detector circuit of the embodiment of the present invention.
Figure 6A:
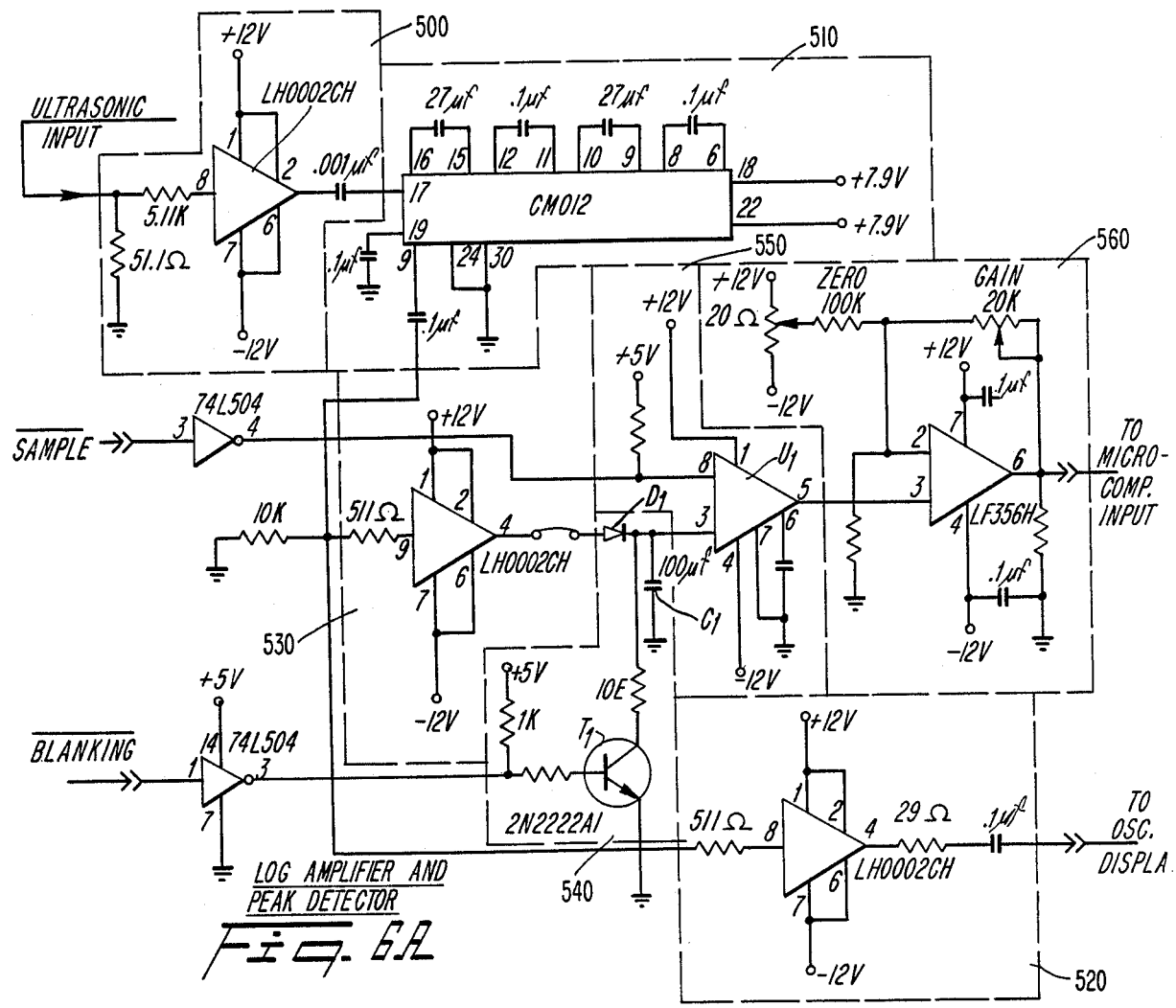
Figure 7:
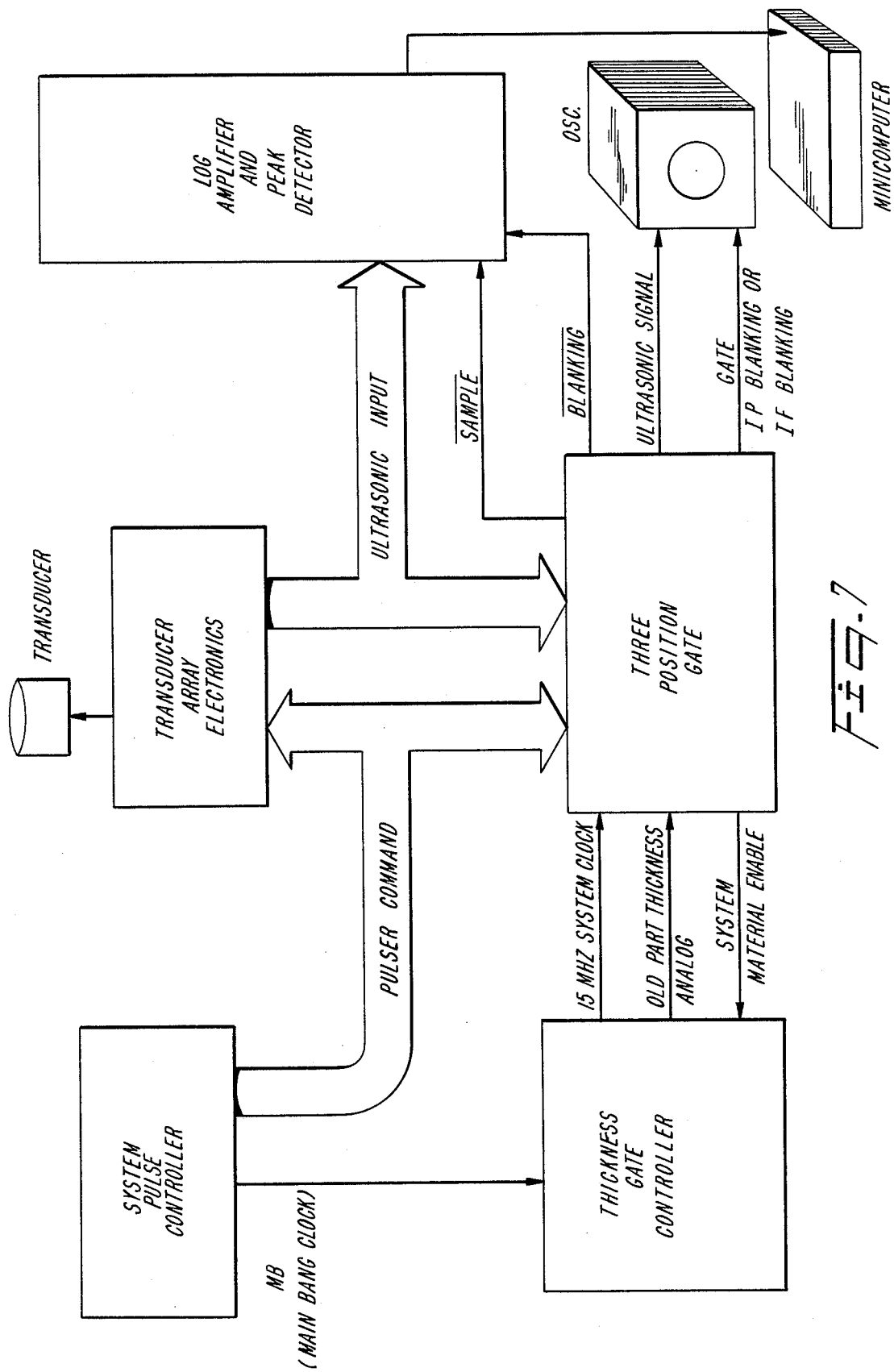
FIG. 7 is a system diagram of the present invention.

FIGS. 2–7 relate to a preferred embodiment of the ultrasonic testing apparatus of the present invention. FIG. 7 is a system diagram which shows system elements and their interrelationship, and FIGS. 2–6 show each element of the system in detail. The block elements in each of the block diagrams (FIGS. 2–6) correspond to the simiarly numbered components shown by the dotted lines around certain circuit elements in the corresponding circuit diagrams (FIGS. 2A–6A).

FIGS. 2–7 show that there are five major components of the system. The System Pulse Controller (FIGS. 2 and 2A) generates the initial timing for the system and there is one of these components per system. In response to controls set on a panel, the System Pulse Controller generates an MB (Main Bang) Clock and $\overline{\text{PULSER COMMAND}}$ (hereafter referred to without the inverting bar) signals. The MB Clock signal period is the same as the time between transmissions of ultrasonic pulses into the element or part under test. The PULSER COMMAND signals each correspond to a different transducer channel and are used both to activate the transmitted ultrasonic pulse for that channel, and to synchronize the operation of the channel electronics with remainder of the system.

The second major system component is the Transducer Array Electronics (FIGS. 3 and 3A) which provides the electrical interfacing of the system with the transducer. In the present embodiment, there is one of these components as shown in FIGS. 3 and 3A for each channel used. The Transducer Array Electronics responds to the corresponding PULSER COMMAND signal to generate a high voltage pulse that drives an ultrasonic transducer to transmit an ultrasonic pulse toward the part or element. The electronics also receives the transduced ultrasonic reflections (or transmissions in the TTU mode) of that pulse and creates the Ultrasonic Input Signal which is then analyzed for defect testing.

The third major system component is the Three-position Gate (FIGS. 4 and 4A) which generates timing signals for a corresponding transducer channel. Each of these Gates corresponds to a different transducer channel. The Three-position Gate receives the PULSER COMMAND and Ultrasonic Input Signal corresponding to the same transducer channel. The Gates for all the transducer channels generate a Blanking signal (shown in its inverted form in the figures) which is used primarily for eliminating unwanted signals from the corresponding oscilloscope trace, and for ensuring that the peak detection circuitry, described below, tests the correct portion of the Ultrasonic Input Signal. The Three-position Gate also receives two other signals: a 15 MHz System clock and an Old Part Thickness Analog signal. The second of those signals is an analog voltage whose level corresponds to the determined part thickness. From the System clock and the Old Part Thickness Analog signal, the Three-position Gate generates two signals which are the inverse of each other.

The $\overline{\text{GATE}}$ signal is used for the oscilloscope display and the $\overline{\text{SAMPLE}}$ signal is used to control the time window during which the Ultrasonic Input is measured. The Three-position Gate corresponding to the thickness transducer signal also generates the System Material Enable signal, which is a pulse whose duration corresponds with the current estimate for the thickness of the part under investigation.

The fourth system component, called the Thickness Gate Controller (FIGS. 5A and 5B), generates the 15 MHz System Clock and the Old Part Thickness Analog signal used by the Three-position Gates. There is only one Thickness Controller in the preferred embodiment. This element compares the current Old Part Thickness Analog signal with voltages representing new thickness estimates which are derived from the System Material Enable signal. If the new estimate differs from the Old Part Thickness Analog signal by less than a predetermined amount, for example, 5%, the Thickness Controller updates the Old Part Thickness Analog voltage signal by replacing that signal with the new estimate.

The fifth component is called the Log Amplifier and Peak Detection circuit (FIGS. 6A and 6B), and there is one of these for each channel. This element processes the Ultrasonic Input signal for display on a visual display device, such as an oscilloscope, and also for detection of defects. The Log Amplifier and Peak Detection circuit also examines the peaks of that signal within a time window depending upon the $\overline{\text{SAMPLE}}$ pulse. The measured peaks during the time window are then sent to a microcomputer in a preferred embodiment for further evaluation.

With this overall system viewpoint, the specific operations of each one of these elements will be easier to understand. The detailed circuit diagrams for each element are shown, but not described in detail because persons of ordinary skill in the art will, from the diagrams, know the details of such circuit operation. In addition, the system shown has eleven (11) transducer channels, but it should be understood that either a fewer or a greater number of transducer channels could also be used consistent with the present invention.

Figure 1A:
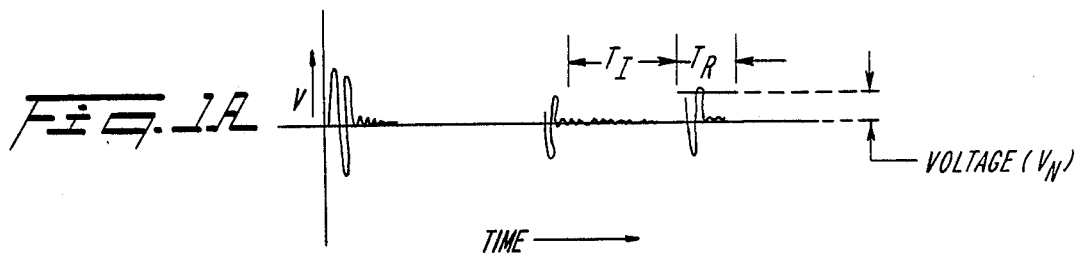
FIGS. 1A and 1B are representations of voltages corresponding to ultrasonic reflections received from a part under inspection.
Figure 1B:
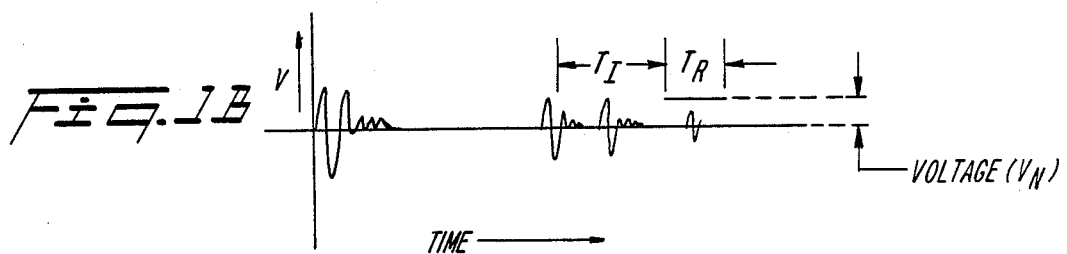
Figure 2:
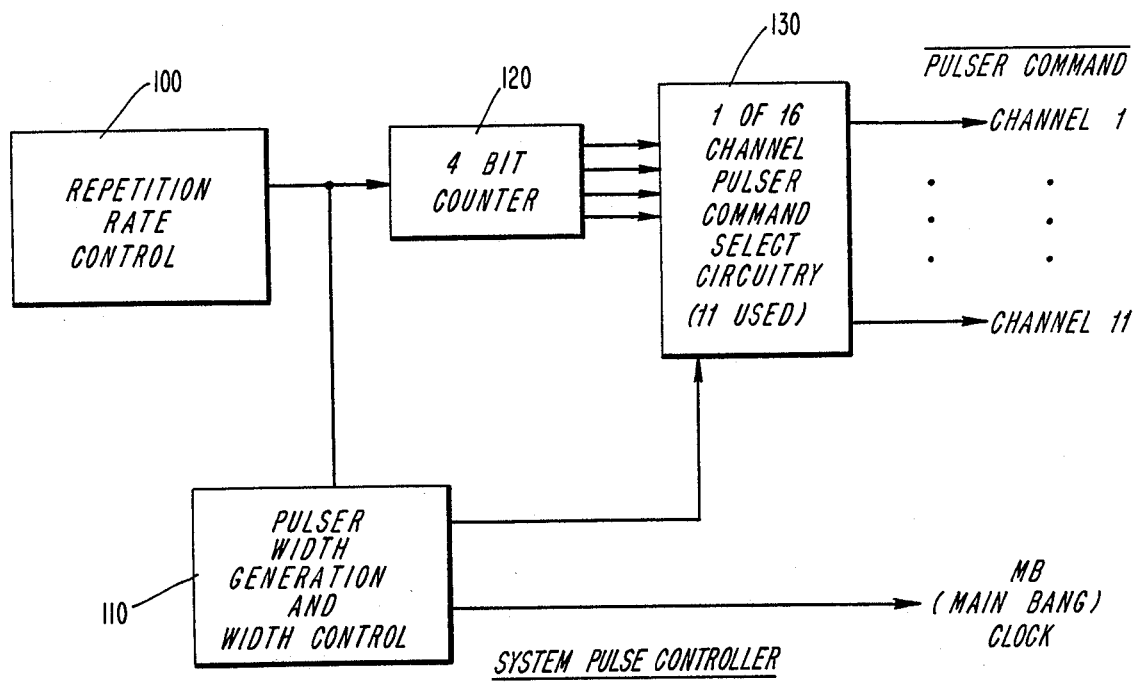

In accordance with the present invention, the apparatus for ultrasonic inspection of a part of this invention includes means for generating a transmission signal. In the preferred embodiment of the invention shown in the figures, the System Pulse Controller shown in FIGS. 2 and 2A includes circuitry for generating a main transmission signal, called the MB clock, and transmission signals for each channel, called PULSER COMMAND signals. Repetition rate controller 100 determines the rate of the MB Clock signal, which is the rate at which ultrasonic transmission pulses are generated. In FIG. 2A, which is the detailed circuit representation of the system pulse control in FIG. 2, IC1 outputs a pulse at a rate which depends upon the value of potentiometer VR1. Potentiometer VR1 is panel-mounted and set by the operator of the system.

Coupled to the output of the repetition rate controller 100 is pulse width generation and width control circuitry 110 which controls the duration of the transmission pulses. The duration of the transmission pulses is related to the amount of ultrasonic energy that is transmitted into the part. FIG. 2A shows that the specific circuitry for control circuitry 110 includes two "one-shots" (also called monostable multivibrators) IC4 and IC5. When triggered by the output of IC1, IC4 generates a one microsecond pulse which is used to trigger IC5. IC5 generates two pulses having opposite polarities. The duration of those pulses is between 50 nanoseconds and 1.7 microseconds. The specific width of the pulse depends upon the setting of potentiometer VR2. The positive-going one of the two pulses is the MB Clock signal.

The remaining two elements shown in the System Pulser Controller of FIGS. 2 and 2A are four bit counter 120 and channel select circuitry 130. Counter 120 receives the output of the repetition rate controller and generates a four-bit binary count that repeats cyclically. Channel select circuitry 130 includes a demultiplexer IC3 which receives the count output from IC2 and sequentially generates single pulses, in order, from each of the output. Each of those pulses serves as one input to a different NOR gate 135 in circuitry 130, each such NOR gate 135 corresponding to one of the channels. The other input to each of gates 135 is the inverse of the MB Clock signal. The output of each NOR gate 135 is a PULSER COMMAND signal for a different one of the transducer channels. The PULSER COMMAND signal is a pulse with a width equal to that of the MB Clock signal.

Corresponding to each transducer channel is a Transducer Array Electronics system as shown in FIGS. 3 and 3A. The systems are used to generate a high voltage signal to drive an ultrasonic transducer in response to the corresponding PULSER COMMAND signal, and also to generate an Ultrasonic Input signal from the reflections received by the transducer.

The transmission electronics includes TTL buffer 200 to isolate the PULSER COMMAND signal from the remainder of the circuitry, and a MOS/FET Driver 210 to interface the PULSER COMMAND signal with a MOS/FET High Voltage Transistor Switch 220. Transistor Switch 220 generates a high voltage pulse to drive the ultrasonic transducer with a pulse whose duration is equal to the duration of the PULSER COMMAND signal.

Ultrasonic receive electronics 230 are coupled to the output of the transducer and change the voltage signals from that transducer into signals of the proper level for further signal processing. If this invention is used in the LOB or PE mode, then only one transducer per channel is used, and the jumper, denoted by the dotted line, is put in place to couple that transducer to the ultrasonic receiver electronics 230. If the system is in the TTU mode, then the jumper is not used, but instead the receiver input comes from the second transducer, located on the opposite side of the part from the transmission transducer, and which is connected to amplifier 230 via the dotted line.

Once the ultrasonic signals have been received and properly amplified, then they must be examined to sense the presence of defects. Accordingly, the present invention includes means for measuring the amplitude of the electrical reflection signals from the transducer channels only during a determined time window. That time window corresponds to a part thickness value that represents the thickness of the part at a portion adjacent to the thickness channel transducer. In the preferred embodiment, the Log Amplifier and Peak Detection circuitry shown in FIGS. 6 and 6A provide for the measurement of the peaks of the corresponding Ultrasonic Input Signal during a time window determined from the Blanking and SAMPLE signals.

In the system and circuitry shown in FIGS. 6 and 6A, Peak Detector 540 receives the corresponding Ultrasonic Input signal from amplifier 230 shown in FIGS. 3 and 3A. The Ultrasonic Input signal is conditioned by a 50 ohm termination analog buffer 500, a log amplifier 510, and an analog buffer 530 before being analyzed by peak detector 540. The purpose of log amplifier 510 is to compress the Ultrasonic Input signal into a signal range of 0-10 volts. Typically, log amplifier 510 provides an 80 dB dynamic range, but persons of ordinary skill in the art will recognize that the dynamic range of such an amplifier is adjustable. The output of log amplifier 510 is also fed via analog buffer 520 to an oscilloscope display for viewing.

As shown in greater detail in FIGS. 6A, peak detector 540 includes capacitor C1 with diode D1 to ensure that C1 charges up to the highest (i.e., peak) input value when a transistor T1 is off. When transistor T1 is on, it shorts C1 to ground and prevents it from charging up. Transistor T1 is controlled by the Blanking signal.

The output of peak detector 540 feeds sample and hold circuit 550. The purpose of sample and hold circuit 550 is to hold the voltage of capacitor C1 at the time period when the SAMPLE signal is active. The end of the active period of the Sample signal corresponds to the end of the time window described above. In this manner, peak detector circuit 540 and sample and hold circuit 550 ensure that the peak of the Ultrasonic Input signal is measured only during a certain time window corresponding to the local thickness of the part under investigation.

The log amplifier and peak detector circuitry in FIGS. 6 and 6A also includes an amplifier 560 to adjust the output of sample and hold circuit 550 to the proper voltage range and current drive for input to a microcomputer unit having an analog/digital converter input (see FIG. 7). The purpose of the microcomputer, which could instead be any type of appropriate analysis equipment depending upon the system's requirements, is for acquiring and displaying data for defect analysis. Of course, the microcomputer may also perform whatever signal analysis is desired.

In accordance with the present invention, the apparatus for ultrasonic inspection of a part also includes thickness gating means for automatically adjusting the thickness value, and thereby the time window, for the measuring means according to electrical reflection signals received by the thickness transducer channel. In the embodiment shown in FIGS. 2-7, the Three-position Gate in FIGS. 4 and 4A and the Thickness Gate Controller in FIGS. 5 and 5A adjust a thickness value, which is called the Old Part Thickness Analog value and is an analog voltage representation of the local part thickness. The adjustment of that level involves the use of a System Material Enable signal, which is a pulse whose duration relates to the part thickness.

According to one variant of this invention, the thickness gating means includes adjustable means for presetting the part thickness value. A setup procedure is shown in FIG. 8, and will be explained along with certain specific circuit elements of the Three-position Gate and Thickness Gate Controller.

In the initialization step, the Ultrasonic Signal is adjusted by placing switch 360 in the IF SYNC mode (step 605). As soon as the signal strength is sufficient (steps 610 and 620), switch 360 is changed to the GATE or thickness sync modes (Step 630).

Next, the IP sync adjustment potentiometer, which is VR-3 in FIG. 4A, is set so that the oscilloscope display of the GATE signal (which, according to the switch setting, is the IP Sync Signal) shows a high-to-low transition before the display reflection from the front surface (step 640). The purpose of the IP sync signal is to eliminate interference either from the Main Bang transmission pulse, from reflector plates, or from any other source of interference that would cause receipt of reflection prior to the receipt of the front surface reflection.

Next, the IF blanking adjustment is set by aligning the transducer with a thinner section of the part to be inspected and then using the IF sync adjustment potentiometer VR4 in FIG. 4A to move a low-to-high transition just after the display of the front surface reflection (steps 650 and 660). Finally, the Initialize button is pressed (step 670) which causes an initial thickness value to be entered into old part thickness value D/A circuit 460, shown in FIGS. 5 and 5A, in a manner to be described below. After this procedure, the ultrasonic apparatus of this invention is now ready for operation.

Figure 4:
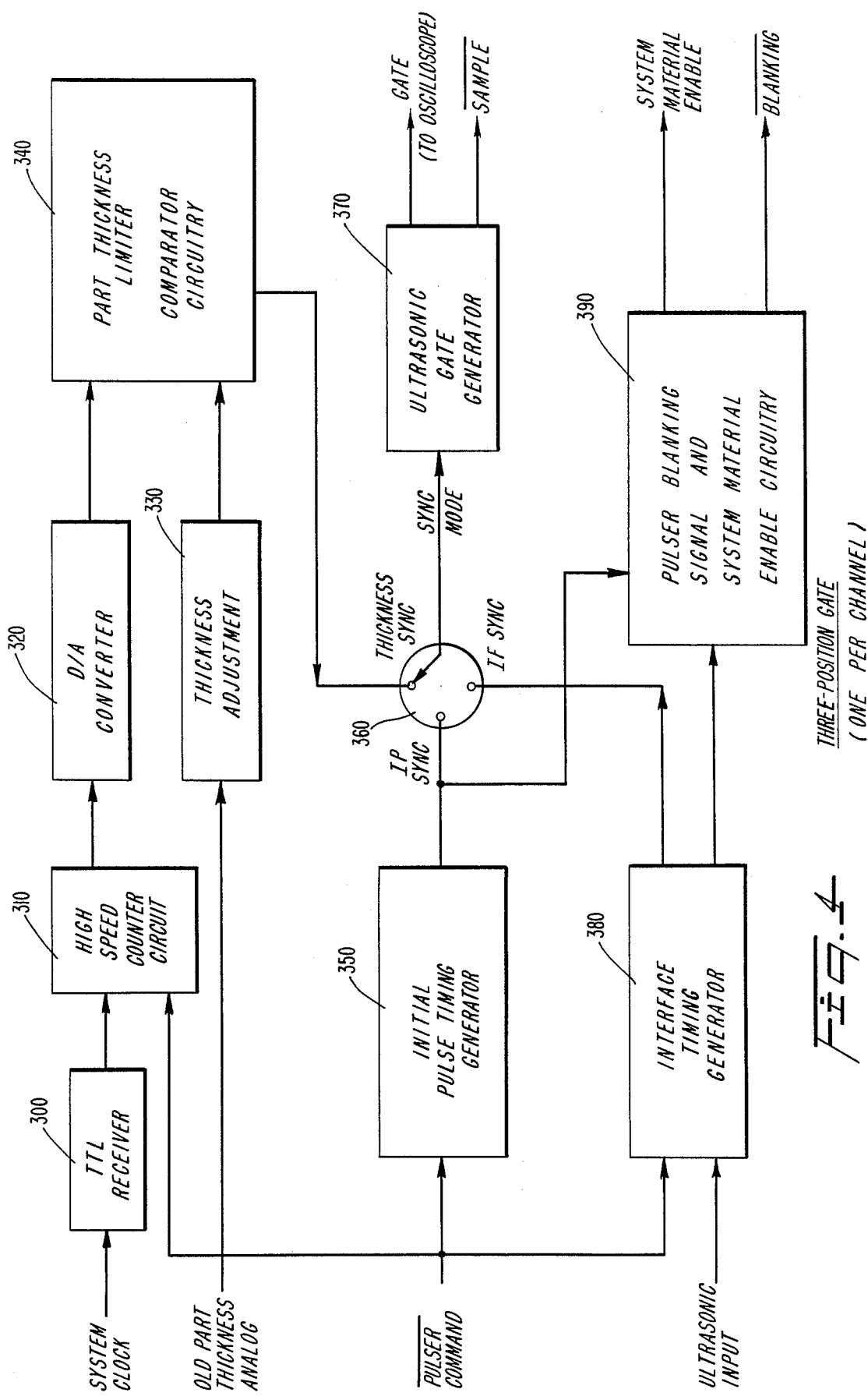
Figure 5A:
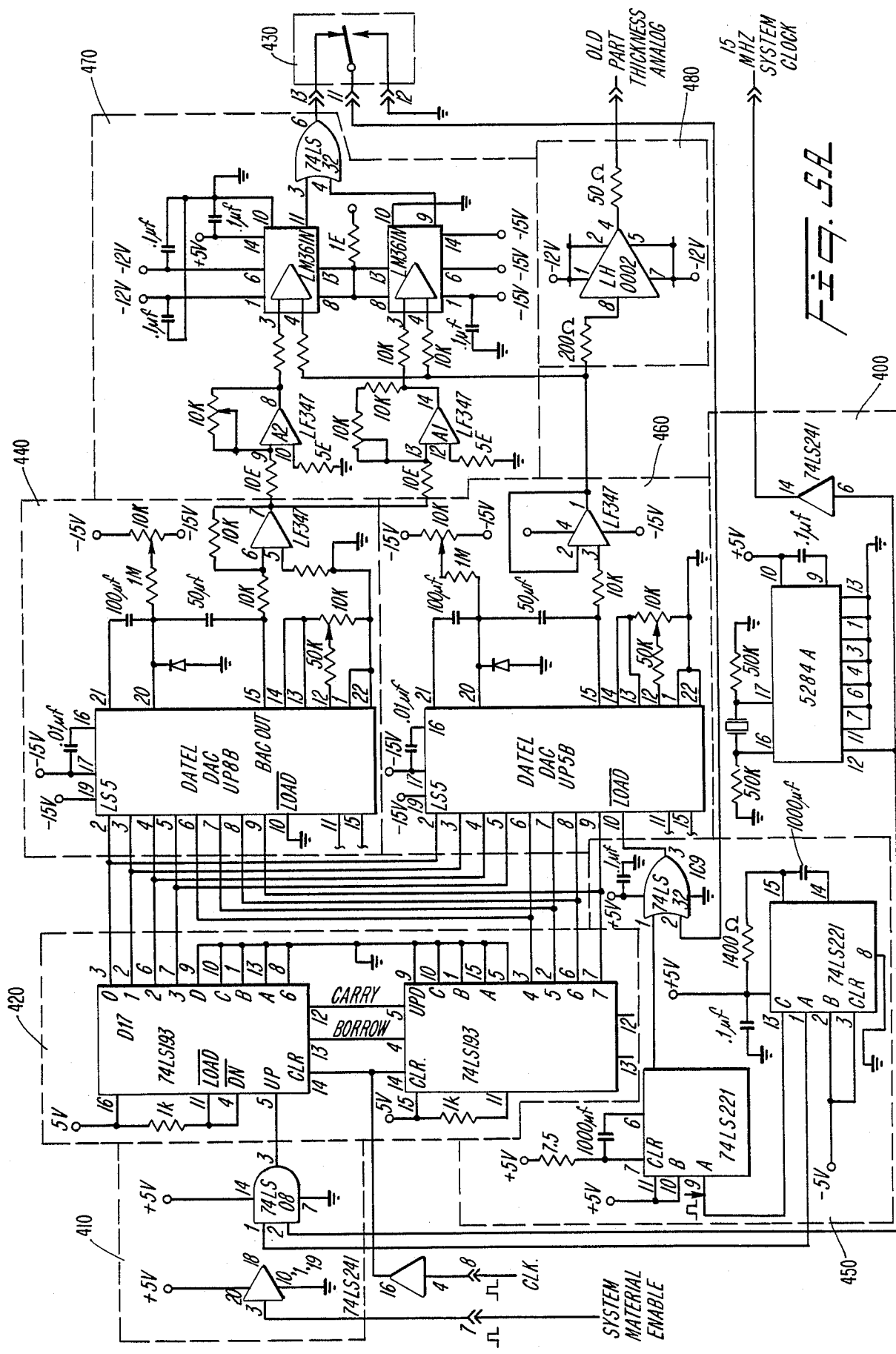

As shown in FIGS. 4 and 4A, the System Clock, which is a 15 MHz clock generated in the Thickness Gate Controller, passes through a TTL receiver 300 and a causes high speed counter 310 to begin counting. Counter circuit 310 had previously been cleared by the appropriate PULSER COMMAND. The output of counter circuit 310 then feeds a digital/analog converter 320 which generates a ramp voltage that tracks the count and has a level corresponding to the period of time elapsed since the PULSER COMMAND.

The Old Part Thickness Analog Voltage signal, which, as indicated above, is a voltage signal whose level represents the currently-determined thickness of the part, is fed through a thickness adjustment circuit 330. Circuit 330 allows an operator to adjust the Old Part Thickness Analog Input to a comparator 340. The ramp voltage and the adjusted Old Part Thickness Analog signal both feed part thickness limiter comparator circuitry 340 shown in FIGS. 4 and 4A.

In the preferred embodiment and as shown in FIG. 4A, comparator 340 includes a monolithic chip comparator IC6 whose output changes state when the ramp voltage exceeds the adjusted Old Part Thickness Analog voltage. The system, and the thickness adjustment circuit 330, are set so that IC6's state change occurs just prior to the anticipated receipt of a rear surface reflection, that anticipated time being based on the believed thickness of the material as reflected in the Old Part Thickness Analog signal.

The output of comparator 340 then feeds ultrasonic gate generator 370, assuming that switch 360 is properly set to the thickness sync mode, to cause the generation of the GATE and SAMPLE signals. Both signals have a predetermined duration determined by "one-shot" IC9. The SAMPLE signal corresponds to the time window for measuring the peak amplitude, since it is a pulse which last from a time just prior to the anticipated receipt of a rear surface reflection, and which remains high for a predetermined period of time sufficient to allow capture of the entire anticipated rear surface reflection. Each channel generates a GATE and SAMPLE signal.

In the preferred embodiment, the Three-Position Gate also generates for each channel a Blanking signal used with the oscilloscope display of the corresponding Ultrasonic Input signal. Only the thickness transducer channel, however, generates a System Material Enable signal and a Blanking signal for use in subsequent timing. The Blanking signal for use in subsequent timing is shown in FIG. 4A as being generated by the flip-flop labelled IC7.

In accordance with the present invention, the thickness gating means of this invention includes means for evaluating the electrical reflection signals received by the thickness transducer channel to determine a part thickness estimate. The System Material Enable signal in the preferred embodiment of this invention may be thought of as a part thickness estimate. That signal is generated by signals received from interface timing generator 380 shown in FIGS. 4 and 4A. Interface timing generator 380 includes IC8 which is a monolithic chip comparator that compares the Ultrasonic Input signal with a threshold value set using potentiometer VR-5. A high output from IC8 means that the Ultrasonic Input signal has exceeded the threshold. The first time that this occurs after the PULSER COMMAND signal corresponds to the received reflection from the front surface and causes the System Material Enable signal goes from a low to a high level. The next time that IC8 generates a pulse, which would correspond to receipt of reflections either from the rear surface or from a defect, the System Material Enable signal drops from a high to a low level. The "thickness estimate" represented by the pulse duration of the System Material Enable signal, will either represent a new thickness measurement or the distance between the front surface and a defect. To determine which value the System Material Enable signals represents, it is compared to the current thickness value represented by the Old Part Thickness Analog signal.

According to the present invention, there is means for replacing the part thickness value with the part thickness estimate when the part thickness value and estimate bear a predetermined relationship with each offer. In the preferred embodiment, the testing of the thickness part estimate and Old Part Thickness Analog signal is performed by the Thickness Gate Controller shown in FIGS. 5 and 5A. As seen in those figures, the System Material Enable signal causes the counter enable 410 to gate the 15 MHz System Clock signals to binary counter 420. The final count of counter 420 represents the number of System Clock pulses which are gated through to the counter during the System Material Enable signal. That final binary count is the input to Part Thickness Estimate D/A circuit 440, whose analog voltage output reflects that final count.

A digital value corresponding to the Old Part Thickness Analog signal has previously been stored in a register internal to the old part thickness value D/A circuit 460. That value was initially input when the Initialize button 430 was pushed, which activated the load input to circuit 460 and caused it to store the binary count generated during the initialization. Thereafter, the digital value in the old part thickness value D/A circuit 460 is periodically updated as described below.

The output of the old part thickness value D/A circuit 460 represents the Old Part Thickness Analog level, which is also made available to the Three-position Gate via Analog Voltage Buffer 480. The Old Part Thickness Analog signal and the part thickness estimate are input to the part thickness comparator circuitry 470 which is shown in greater detail in FIG. 5A. In the embodiment shown in FIG. 5A, the part thickness estimate is fed through amplifiers A1 and A2, which multiply the part thickness estimate by values greater and less than unity, respectively. Preferably those values are 1.05 and 0.95, which represent a ±5% deviation, but the potentiometers in the feedback circuit for amplifiers A1 and A2 may be adjusted for different values. These multiple values are inputs to part thickness comparator circuitry 470 along with the Old Part Thickness Analog signal. If the part thickness estimate is greater than 0.95 and less than 1.05 the Old Part Thickness Analog level (or within other limits if the ±5% deviation are not used), then the output of part thickness comparator circuitry 470 changes state and cause new part thickness "valid" pulse generator 450 to load the digital output of counter 420, which corresponds to the part thickness estimate, into old part thickness value D/A circuit 460. This causes an updating of the Old Part Thickness Analog value. If, however, the part thickness estimate is outside of the predetermined range, then the Old Part Thickness Value stored in circuit 460 remains the same.

Figure 9:
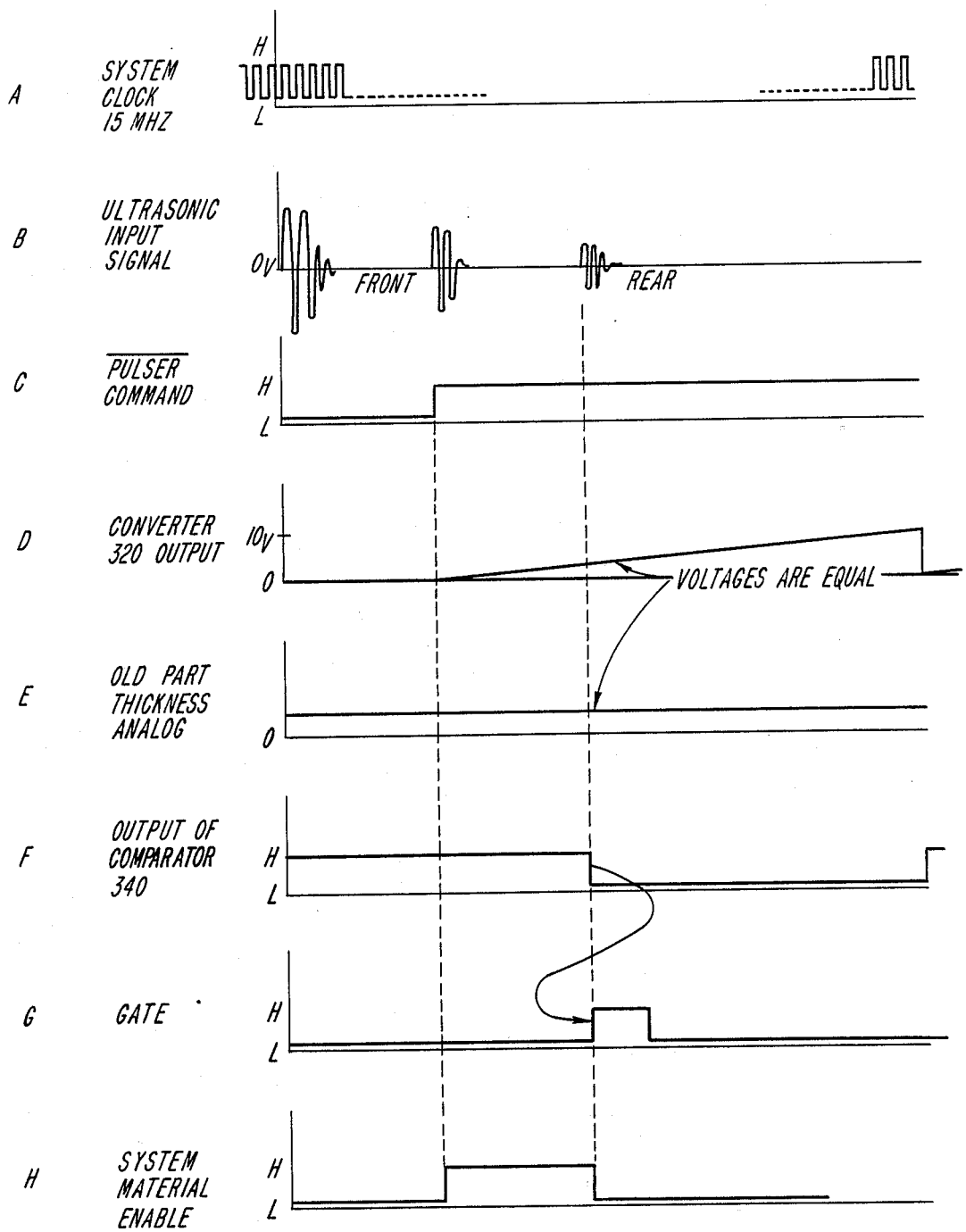
FIG. 9 is a timing diagram for explanation of the operation of the embodiment of the present invention.

FIG. 9 shows the timing relationship of the signals just discussed. FIG. 9A is the System Clock, FIG. 9B is the Ultrasonic Input Signal, FIG. 9C is the $\overline{\text{PULSER COMMAND}}$, FIG. 9D is the output of D/A converter 320, FIG. 9F is the Old Part Thickness Analog signal, and FIG. 9F is the output of the comparator 340, which switches state when the signals 9D and 9E (as adjusted) are equal, i.e. at voltage $V_t$. As described above, this equality causes the generation of the GATE (and SAMPLE) signal as shown in FIG. 9G. FIG. 9H is the System Material Enable signal.

It will be apparent to those skilled in the art that modifications and variations can be made in the ultrasonic inspection apparatus and methods of this invention. The invention in its broader aspects is not limited to the specific details, representative methods and apparatus, and illustrative examples shown and described. Departure may be made from such details without departing from the spirit or scope of the general inventive concept.

What is claimed is:

1. An apparatus for ultrasonic inspection of a part comprising:
    means for generating a transmission signal;
    a plurality of transducer channels, coupled to said transmission signal generating means, for generating ultrasonic pulses for transmission into said part, for receiving portions of said ultrasonic pulses from said part, and for creating electrical reflection signals representing said portions, one of said transducer channels being a thickness transducer channel and including means for determining a part thickness value representing the thickness of a portion of said part adjacent said thickness transducer channel;
    means, coupled to each of said transducer channels, for measuring the amplitude of said electrical reflection signals only during a time window corresponding to said part thickness value; and
    thickness gating means, coupled to said measuring means, for automatically replacing said part thickness value with a subsequently determined part thickness value, and thereby adjusting said time window, according to electrical reflection signals received by said thickness transducer channel only if said subsequently determined part thickness value differs from said part thickness value by less than a predetermined difference value.

2. The apparatus of claim 1 wherein said thickness gating means includes:
    adjustable means for presetting said part thickness value;
    means for evaluating said electrical reflection signals received by said thickness transducer channel to determine a part thickness estimate; and
    means for replacing said part thickness value with said part thickness estimate when said part thickness value and said part thickness estimate bear a predetermined relationship with each other.

3. The apparatus of claim 2 further including
    a visual display device coupled to at least one of said transducer channels for displaying said electrical reflection signals; and
    means, coupled to said display device, for generating a blanking signal having a duration related to the onset of said transmission signal and the receipt of said first major signal portion for blanking out from said display a corresponding portion of said displayed electrical reflection signals.

4. The apparatus of claim 2 wherein portions of said electrical reflection signals having amplitudes greater than a predetermined threshold are termed major reflection portions and wherein said evaluating means includes
    means for selecting from said thickness transducer channel's electrical reflection signals a first major signal portion representing the front surface of said part;
    means for selecting from said thickness transducer channel's electrical reflection signals a second major signal portion, received after said first signal portion; and
    means for forming said part thickness estimate from the time difference between receipt of said first major signal portion and said second major signal portion.

5. The apparatus of claim 4 wherein said replacing means includes:
    means for storing said part thickness value;
    means for generating a representation of said part thickness estimate;
    means for comparing said said part thickness estimate representation and said stored part thickness value and for generating a comparison signal if said part thickness value and said part thickness estimate bear said predetermined relationship with each other; and
    mens, responsive to said comparison signal, for storing said part thickness estimate in said storing means, thereby replacing said part thickness value with said part thickness estimate.

6. The apparatus of claim 5 wherein said comparing means includes a amplifier circuit to multiply said part thickness estimate by values corresponding to said predetermined relationship.

7. The apparatus of claim 5 wherein said thickness gating means also includes
    means for generating a ramp signal related to the time elapsed from the onset of said transmission signal; and
    means for comparing said ramp signal to said part thickness value to generate a sample pulse representing said time window.

8. The apparatus of claim 7 wherein said measuring means includes a peak detector circuit coupled to said comparing means for determining the peak value of said electrical reference signals received by said transducer channels.

9. The apparatus of claim 8 wherein said measuring means also includes a computer.

10. The apparatus of claim 1 further including
a visual display device coupled to at least one of said transducer channels for displaying said electrical reflection signals; and
means, coupled to said display device, for generating a blanking signal to blank out a portion of said displayed electrical reflection signals.

11. The apparatus of claim 1 wherein said measuring means includes a logarithmic amplifier for adjusting the dynamic range of said electrical reflection signals.

12. A method of nondestructive ultrasonic testing of a part comprising the steps of:
generating a transmission signal;
transmitting ultrasonic pulses into said part using a plurality of transducer channels;
receiving and transducing portions of said ultrasonic pulses and creating electrical reflection signals representing those portions;
determining, from one of said transducer channels being termed a thickness transducer channel, a part thickness value representing the thickness of a portion of said part adjacent said thickness transducer channel;
measuring the amplitude of said electrical reflection signals only during a time window corresponding to said part thickness value; and
automatically replacing said part thickness value with a subsequently determined part thickness value, and thereby adjusting said time window, according to electrical reflection signals received by said thickness transducer channel only if said subsequently determined part thickness value differs from said part thickness value by less than a predetermined difference value.

13. The method in claim 12 wherein said step of automatic adjusting includes the steps of:
presetting said part thickness value;
evaluating said electrical reflection signals received by said thickness transducer channel to determine a part thickness estimate; and
replacing said part thickness value with said part thickness estimate when said part thickness value and said part thickness estimate bear a predetermined relationship with each other.

14. The method of claim 13 wherein portions of said electrical signals having amplitudes greater than a predetermined threshold are termed major reflection portions, and
wherein said evaluating step includes the steps of:
selecting from said thickness transducer channel's electrical reflection signals a first major signal portion representing the front surface of said part;
selecting from said thickness transducer channel's electrical reflection signals a second major signal portion received after said first signal portion; and
forming said part thickness estimate from the time difference between receipt of said first major signal portion and said second major signal portion.

15. The method of claim 14 wherein said replacing step includes the steps of:
storing said part thickness value;
generating a representation of said part thickness estimate;
comparing said representation of said part thickness estimate and said part thickness value;
generating a comparison signal if said part thickness value and said part thickness estimate representation bear said predetermined relationship with each other; and
storing said part thickness estimate in said storing means in response to said comparison signal, thereby replacing said part thickness value with said part thickness estimate.

16. The method of claim 15 wherein said automatic adjusting step includes the steps of:
generating an analog ramp signal related to the time elapsed from the onset of said transmission signal; and
comparing said analog ramp signal to said part thickness value to generate a sample pulse representing said time window.

17. The method of claim 16 wherein said measuring step includes the step of determining the peak value of said electrical reference signals received by said transducer channels during said sample pulse duration; and
wherein said comparing step includes the step of generating said sample pulse with a predetermined time duration.

18. The method of claim 17 further including the steps of displaying said electrical reflection signals for at least one transducer channel; and
generating a blanking signal to prevent displaying unwanted portions of said displayed electrical reflection signals, and
wherein said replacing step includes the steps of:
storing said part thickness value;
generating an analog voltage level representing said part thickness estimate;
comparing said analog voltage level representing said part thickness estimate and said part thickness value;
generating a comparison signal if said part thickness value and said part thickness estimate analog voltage levels bear said predetermined relationship with each other; and
storing said part thickness estimate in said storing means in response to said comparison signal, thereby replacing said part thickness value with said part thickness estimate.

19. An apparatus for ultrasonic inspection of a part comprising:
means for generating a transmission signal;
a plurality of transducer channels, coupled to said transmission signal generating means, for generating ultrasonic pulses for transmission into said part, for receiving ultrasonic pulses from said part, and for creating electrical reflection signals representing said pulses, those portions of said electrical reflection signals having amplitudes greater than a predetermined threshold being termed major reflection portions, one of said transducer channels being a thickness transducer channel and including means for determining a value representing the thickness of a portion of said part adjacent said thickness transducer channel;
thickness gating means for automatically adjusting said part thickness value, and thereby a time window, according to electrical reflection signals received by said thickness transducer channel, said thickness gating means including:
adjustable means for presetting said part thickness value;
means for evaluating said electrical reflection signals received by said thickness transducer channel to determine a part thickness estimate, said evaluating means including means for selecting from said thickness transducer channel's electrical reflection signals a first major signal portion representing the front surface of said part;

means for selecting from said thickness transducer channel's electrical reflection signals a second major signal portion, received after said first signal portion; and means for forming said part thickness estimate from the time difference between receipt of said first major signal portion and said second major signal portion;

means for replacing said part thickness value with said part thickness estimate when said part thickness value and said part thickness estimate bear a predetermined relationship with each other, said replacing means including means for storing said part thickness value;

means for generating a representation of said part thickness estimate;

means for comparing said said part thickness estimate representation and said stored part thickness value and for generating a comparison signal if said part thickness value and said part thickness estimate bear said predetermined relationship with each other; and means, responsive to said comparison signal, for storing said part thickness estimate in said storing means, thereby replacing said part thickness value with said part thickness estimate;

means for generating a ramp signal related to the time elapsed from the onset of said transmission signal; and means for comparing said ramp signal to said part thickness value to generate a sample pulse representing said time window, said ramp signal comparing means including a monostable multivibrator for generating said sample pulse with a predetermined time duration; and means, coupled to each of said transducer channels and to said thickness gating means, for measuring the amplitude of said electrical reflection signals only during a time window corresponding to said part thickness value, said measuring means including a peak detector circuit coupled to said comparing means for determining the peak value of said electrical reference signals received by said transducer channels and including means for being activated only during said predetermined time duration.

20. An apparatus for ultrasonic inspection of a part comprising:

means for generating a transmission signal;

a plurality of transducer channels, coupled to said transmission signal generating means, for generating ultrasonic pulses for transmission into said part, for receiving said ultrasonic pulses from said part, and for creating electrical reflection signals representing said pulses, portions of said electrical reflection signals having amplitudes greater than a predetermined threshold being termed major reflection portions, one of said transducer channels being a thickness transducer channel and including means for determining a value representing the thickness of a portion of said part adjacent said thickness transducer channel;

thickness gating means for automatically adjusting said part thickness value, and thereby a time window, according to electrical reflection signals received by said thickness transducer channel, said thickness gating means including adjustable means for presetting said part thickness value;

means for evaluating said electrical reflection signals received by said thickness transducer channel to determine a part thickness estimate, said evaluating means including means for selecting from said thickness transducer channel's electrical reflection signals a first major signal portion representing the front surface of said part;

means for selecting from said thickness transducer channel's electrical reflection signals a second major signal portion, received after said first signal portion; and means for forming said part thickness estimate from the time difference between receipt of said first major signal portion and said second major signal portion;

means for replacing said part thickness value with said part thickness estimate when said part thickness value and said part thickness estimate bear a predetermined relationship with each other, and means for generating a sample gate signal from said part thickness value, said sample pulse occurring at an estimated time of receipt by said transducer channels of reflections from a rear surface of said part; and means, coupled to each of said transducer channels and to said thickness gating means, for measuring the amplitude of said electrical reflection signals only during a time window corresponding to said part thickness value, said measuring means being activated only during said sample gate signal.

21. The apparatus of claim 20 wherein said plurality of transducer channels each includes two ultrasonic transducers positioned on opposite sides of said part.

22. The apparatus of claim 20 wherein said plurality of transducer channels each includes a single ultrasonic transducer element for generating and receiving said ultrasonic pulses.

23. An apparatus for ultrasonic inspection of a part comprising:

means for generating a transmission signal;

a plurality of transducer channels, coupled to said transmission signal generating means, for generating ultrasonic pulses for transmission into said part, for receiving said ultrasonic pulses from said part, and for creating electrical reflection signals representing said pulses, portions of said electrical reflection signals having amplitudes greater than a predetermined threshold being termed major reflection portions, one of said transducer channels being a thickness transducer channel and including means for determining a value representing the thickness of a portion of said part adjacent said thickness transducer channel;

thickness gating means for automatically adjusting said part thickness, and thereby a time window, according to electrical reflection signals received by said thickness transducer channel, said thickness gating means including adjustable means for presetting said part thickness value;

means for evaluating said electrical reflection signals received by said thickness transducer channel to determine a part thickness estimate, said evaluating means including
- means for selecting from said thickness transducer channel's electrical reflection signals a first major signal portion representing the front surface of said part;
- means for selecting from said thickness transducer channel's electrical reflection signals a second major signal portion, received after said first signal portion; and
- means for forming said part thickness estimate from the time difference between receipt of said first major signal portion and said second major signal portion;

means for replacing said part thickness value with said part thickness estimate when said part thickness value and said part thickness estimate bear a predetermined relationship with each other;

means for generating a sample gate signal from said part thickness value, said sample pulse occurring approximately at the time of receipt by said transducer channels of reflections from the interior portion of said part between a rear surface of said part and said front surface of said part; and means, coupled to each of said transducer channels and to said thickness gating means, for measuring the amplitude of said electrical reflection signals only during a time window corresponding to said part thickness value, said measuring means being activated only during said sample gate signal.

24. The apparatus of claim 23 wherein said plurality of transducer channels each includes two ultrasonic transducers positioned on opposite sides of said part.

25. The apparatus of claim 23 wherein said plurality of transducer channels ech includes a single ultrasonic transducer element for generating and receiving said ultrasonic pulses.

26. An apparatus for ultrasonic inspection of a part comprising:
- means for generating a transmission signal;
- a plurality of transducer channels, coupled to said transmission signal generating means, for generating ultrasonic pulses for transmission into said part, for receiving ultrasonic pulses from said part, and for creating electrical reflection signals representing said pulses, those portions of said electrical reflection signals having amplitudes greater than a predetermined threshold being termed major reflection portions, one of said transducer channels being a thickness transducer channel and including means for determining a value representing the thickness of a portion of said part adjacent said thickness transducer channel; thickness gating means, coupled to said measuring means, for automatically adjusting said part thickness value, and thereby a time window, according to electrical reflection signals received by said thickness transducer channel, said thickness gating means including:
  - adjustable means for presetting said part thickness value;
  - means for evaluating said electrical reflection signals received by said thickness transducer channel to determine a part thickness estimate, said evaluating means including
    - means for selecting froms aid thickness transducer channel's electrical reflection signals a first major signal portion representing the front surface of said part;
    - means for selecting from said thickness transducer channel's electrical reflection signals a second major signal portion, received after said first signal portion; and
    - means for forming said part thickness estimate from the time difference between receipt of said first major signal portion and said second major signal portion;
  - means for replacing said part thickness value with said part thickness estimate when said part thickness value and said part thickness estimate bear a predetermined relationship with each other, said replacing means including
    - means for storing said part thickness value;
    - means for generating a representation of said part thickness estimate;
    - means for comparing said said part thickness estimate representation and said stored part thickness value and for generating a comparison signal if said part thickness value and said part thickness estimate bear said predetermined relationship with each other; and
    - means, responsive to said comparison signal, for storing said part thickness estimate in said storing means, thereby replacing said part thickness value with said part thickness estimate;
  - means for generating a ramp signal related to the time elapsed from the onset of said transmission signal;
  - means for comparing said ramp signal to said part thickness value to generate a sample pulse representing said time window; and
  - means, coupled to each of said transducer channels and to said thickness gating means, for measuring the amplitude of said electrical reflection signals only during a time window corresponding to said part thickness value, said measuring means including a peak detector circuit coupled to said comparing means for determining the peak value of said electrical reference signals received by said transducer channels, said peak detector circuit including:
    - a capacitor coupled to one of said electrical reflection circuits;
    - a transistor, coupled to said capacitor for resetting said capacitor; and
    - a sample and hold circuit coupled to said capacitor and controlled by said sample pulse.

* * * * *

UNITED STATES PATENT AND TRADEMARK OFFICE
CERTIFICATE OF CORRECTION

PATENT NO. : 4,799,177
DATED : January 17, 1989
INVENTOR(S) : Dennis P. Sarr

It is certified that error appears in the above-identified patent and that said Letters Patent is hereby corrected as shown below:

Column 12,
    Claim 6, line 51, change "a amplifier" to --an amplifier--.

Column 15,
    Claim 19, line 21, change "comparing said said part" to --comparing said part--.

Column 16,
    Claim 23, line 61, change "part thickness, and" to --part thickness value, and--.

Column 17,
    Claim 25, line 36, change "ech" to --each--.

Column 18,
    Claim 26, line 27, change "comparing said said part" to --comparing said part--.

Signed and Sealed this

Tenth Day of October, 1989

Attest:

DONALD J. QUIGG

Attesting Officer

Commissioner of Patents and Trademarks